United States Patent
Williams et al.

(10) Patent No.: US 11,039,798 B2
(45) Date of Patent: Jun. 22, 2021

(54) ROTATING STRUCTURE FOR RADIATION IMAGING MODALITIES

(71) Applicant: Analogic Corporation, Peabody, MA (US)

(72) Inventors: Robert Williams, Wilmington, MA (US); Andrew Alvino, Haverhill, MA (US); Ronald E Swain, Reading, MA (US); Tadas Vaisvila, Salem, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 16/336,452

(22) PCT Filed: Sep. 29, 2016

(86) PCT No.: PCT/US2016/054309
§ 371 (c)(1),
(2) Date: Mar. 25, 2019

(87) PCT Pub. No.: WO2018/063210
PCT Pub. Date: Apr. 5, 2018

(65) Prior Publication Data
US 2019/0231281 A1    Aug. 1, 2019

(51) Int. Cl.
*A61B 6/03*          (2006.01)
*A61B 6/00*          (2006.01)
(Continued)

(52) U.S. Cl.
CPC ............ *A61B 6/035* (2013.01); *A61B 6/4429* (2013.01); *F16C 19/183* (2013.01); *F16C 33/61* (2013.01);
(Continued)

(58) Field of Classification Search
CPC .. A61B 6/00; A61B 6/03; A61B 6/035; A61B 6/4429; A61B 6/44; F16C 33/61; F16C 19/18; F16C 19/183; F16C 2300/14
(Continued)

(56) References Cited

U.S. PATENT DOCUMENTS 6,337,894 B1    1/2002  Tybinkowski et al.
8,807,833 B2 *  8/2014  Sharpless ............... A61B 6/035
                                              378/197

(Continued)

FOREIGN PATENT DOCUMENTS

WO     2018/063210 A1    4/2018

OTHER PUBLICATIONS

Written Opinion of the International Searching Authority for PCT Application No. PCT/US2016/054309 dated Jun. 2, 2017, 7 pages.
(Continued)

*Primary Examiner* — Jurie Yun
(74) *Attorney, Agent, or Firm* — TraskBritt

(57) ABSTRACT

Among other things, a computed tomography (CT) imaging modality is provided. The imaging modality includes a radiation source that emits radiation. The imaging modality includes a detector array that detects at least a portion of the radiation. The imaging modality includes a rotating structure that rotates about an axis. The rotating structure includes a first support portion having a first shape. The rotating structure includes a second support portion having a second shape different than the first shape. The radiation source and the detector array are mounted to the second support portion.

21 Claims, 4 Drawing Sheets

(51) Int. Cl.
*F16C 19/18* (2006.01)
*F16C 33/61* (2006.01)

(52) U.S. Cl.
CPC ......... *A61B 6/4085* (2013.01); *F16C 2300/14* (2013.01)

(58) Field of Classification Search
USPC ...................................................... 378/4, 15
See application file for complete search history.

(56) References Cited

U.S. PATENT DOCUMENTS

| | | |
|---|---|---|
| 2011/0058644 A1 | 3/2011 | Thran et al. |
| 2013/0266116 A1 | 10/2013 | Abenaim et al. |
| 2015/0265229 A1 | 9/2015 | Maki et al. |
| 2018/0172854 A1* | 6/2018 | Moore ..................... G01T 7/00 |

OTHER PUBLICATIONS

International Search Report for PCT Application No. PCT/US2016/054309 dated Jun. 2, 2017, 6 pages.

* cited by examiner

ROTATING STRUCTURE FOR RADIATION IMAGING MODALITIES

CROSS-REFERENCE TO RELATED APPLICATIONS

This application is a national phase entry under 35 U.S.C. § 371 of International Patent Application PCT/US2016/054309, filed Sep. 29, 2016, designating the United States of America and published in English as International Patent Publication WO 2018/063210 A1 on Apr. 5, 2018.

TECHNICAL FIELD

The present application relates to a rotating structure for radiation imaging modalities (e.g., imaging modalities that utilize radiation to examine an object). It finds particular application in the context of computed tomography (CT) scanners. However, the features described herein are not intended to be limited to CT applications and/or other radiation imaging applications.

BACKGROUND

Today, CT and other radiation imaging modalities (e.g., mammography, digital radiography, single-photon emission computed tomography, etc.) are useful to provide information, or images, of interior aspects of an object under examination. Generally, the object is exposed to radiation (e.g., X-rays, gamma rays, etc.), and an image(s) is formed based upon the radiation absorbed and/or attenuated by the interior aspects of the object, or rather an amount of radiation photons that is able to pass through the object. Typically, highly dense aspects of the object (or aspects of the object having a composition comprised of higher atomic number elements) absorb and/or attenuate more radiation than less dense aspects, and thus an aspect having a higher density (and/or high atomic number elements), such as a bone or metal, for example, will be apparent when surrounded by less dense aspects, such as muscle or clothing.

Radiation imaging modalities generally comprise, among other things, one or more radiation sources (e.g., an X-ray source, Gamma-ray source, etc.) and a detector array comprised of a plurality of pixels that are respectively configured to convert radiation that has traversed the object into signals that may be processed to produce the image(s). As an object is passed between the radiation source(s) and the detector array, radiation is absorbed/attenuated by the object, causing changes in the amount/energy of detected radiation. Using information derived from the detected radiation, radiation imaging modalities are configured to generate images that can be used to detect items within the object that may be of particular interest (e.g., body characteristics, threat items, etc.). These images may be two-dimensional images or three-dimensional images.

To generate three-dimensional images, at least one of the radiation sources or the detector array is rotated relative to the object under examination to acquire information about the object from various views. In CT scanners, the radiation source(s) and the detector array are typically mounted to a disk or drum that is rotated about the object under examination. These disks or drums must be sized to accommodate the object (e.g., luggage, a human patient, etc.) in a center bore, and thus the outer diameter of such disks or drums may exceed five feet.

Moreover, in some applications, such as in medical applications where minimal movement by the patient is desired during the imaging process applications, these disks or drums must spin at speeds in excess of 100 revolutions per minute (RPM) to shorten the time that the patient is required to be still. At such speeds, the disk or drum may be subjected to relatively large inertial loads that can cause deflection between the radiation source(s) and the detector array. Further, these inertial loads may cause deflection within support bearings of the rotating structure. The algorithms used to reconstruct the images from the information generated about detected radiation rely on a precise alignment between the radiation source(s) and the detector array, and thus such deflection can cause unwanted vibrations that result in reduced image quality.

BRIEF SUMMARY

Aspects of the present application address the above matters, and others. According to one aspect a computed tomography (CT) imaging modality is provided. The imaging modality comprises a radiation source configured to emit radiation and a detector array configured to detect at least a portion of the radiation. The imaging modality further comprises a rotating structure configured to rotate about an axis. The rotating structure comprises a first support portion defining a substantially cylindrical interior cavity. The rotating structure also comprises a second support portion defining a non-cylindrical interior cavity. The radiation source and the detector array are mounted to the second support portion.

According to another aspect, a computer tomography (CT) imaging modality comprises a radiation source configured to emit radiation and a detector array configured to detect at least a portion of the radiation. The imaging modality also comprises a rotating structure configured to rotate about an axis. The rotating structure comprises a first support portion comprising a wall defining a substantially cylindrical interior cavity. The wall of the first support portion has an outer radial surface, diametrically opposing the substantially cylindrical interior cavity, which has a circumference. The rotating structure also comprises a second support portion comprising a wall defining a non-cylindrical interior cavity. The wall of the second support portion comprises a first wall segment having an inner surface that in part defines the non-cylindrical interior cavity. The inner surface of the first wall segment lies in a first plane. The wall of the second support portion comprises a second wall segment having an inner surface that in part defines the non-cylindrical interior cavity. The inner surface of the second wall segment lies in a second plane.

According to another aspect, a computed tomography (CT) imaging modality comprises a radiation source configured to emit radiation and a detector array configured to detect at least a portion of the radiation. The imaging modality also comprises a rotating structure configured to rotate about an axis. The rotating structure comprises a support portion comprising a wall defining a non-cylindrical interior cavity. The wall of the support portion comprises a first wall segment having an inner surface that in part defines the non-cylindrical interior cavity. The inner surface of the first wall segment lies in a first plane. The wall of the support portion comprises a third wall segment having an inner surface that in part defines the non-cylindrical interior cavity. The inner surface of the third wall segment lies in a third plane. The third wall segment diametrically opposes the first wall segment relative to the non-cylindrical interior cavity. The radiation source and detector array lie along a second axis perpendicular to the axis. A distance between the first wall segment and the third wall segment at a first location along the second axis is different than a distance between the first wall segment and the third wall segment at a second location along the second axis.

Those of ordinary skill in the art will appreciate still other aspects of the present application upon reading and understanding the appended description.

BRIEF DESCRIPTION OF THE DRAWINGS

The application is illustrated by way of example and not limitation in the figures of the accompanying drawings, in which like references generally indicate similar elements and in which.

DETAILED DESCRIPTION

Figure 1:
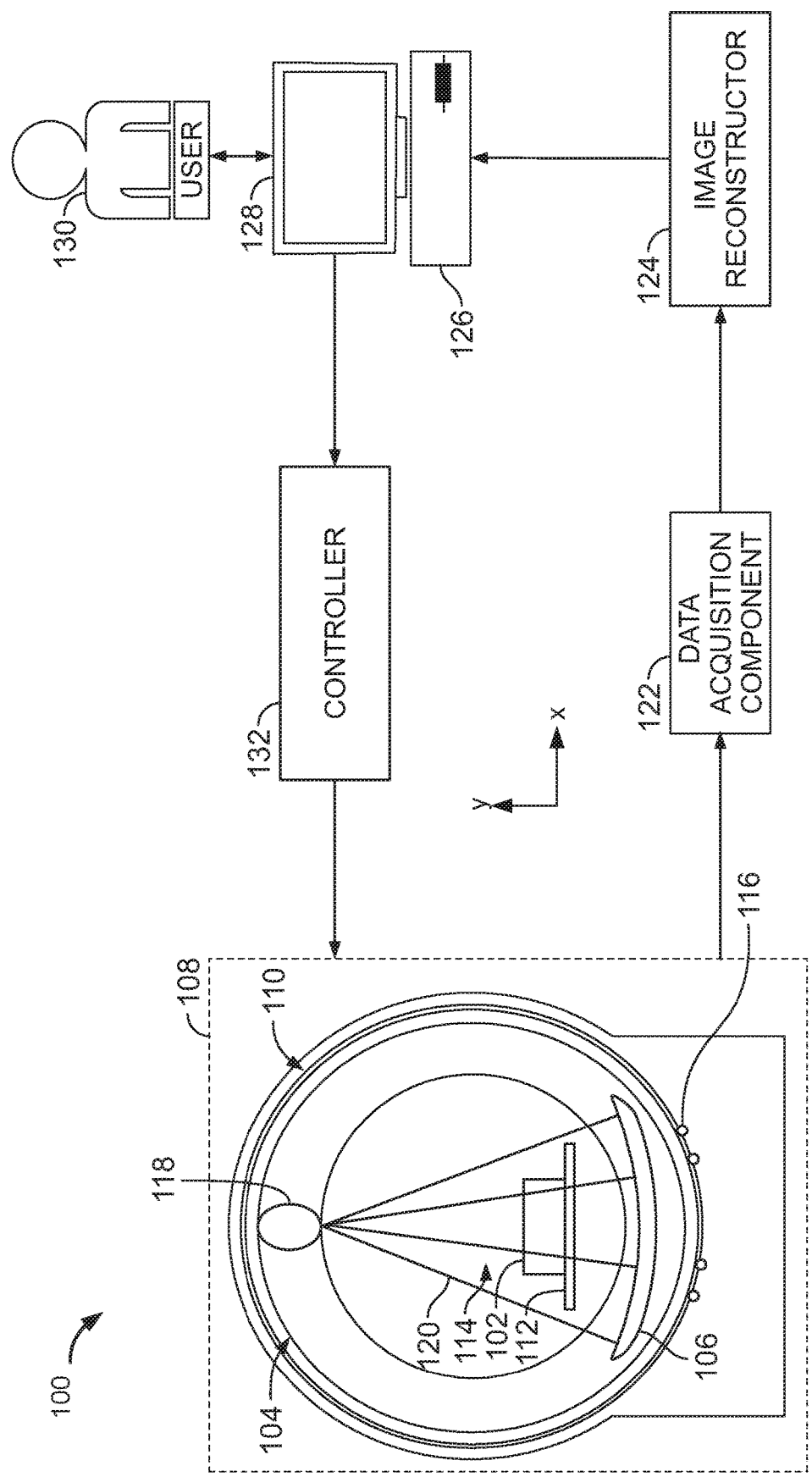
FIG. 1 illustrates an example environment of an imaging modality.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

The present disclosure relates to a rotating structure upon which the radiation source and the detector array are mounted. The rotating structure is shaped so as to reduce deflections in structurally significant regions (e.g., regions of the rotating structure where deflections would be felt by the radiation source and/or detector array). As will be described in more detail throughout the disclosure, the rotating structure comprises a first support portion and a second support portion. In some embodiments, the first support portion is substantially cylindrical. Bearings are mounted to the first support portion and couple the rotating structure to a stationary support structure. In some embodiments, the second support portion is non-cylindrical (e.g., triangular or "A-framed"). The radiation source and the detector array are mounted to the second support portion.

FIG. 1 is an illustration of an example environment 100 comprising an example radiation imaging modality that may be configured to generate data (e.g., images) representative of an object 102 or aspect(s) thereof under examination. It will be appreciated that the features described herein may find applicability to other imaging modalities besides the example computed tomography (CT) scanner illustrated in FIG. 1. For example, the rotating structure 104 described herein may find applicability to other types of radiation imaging modalities, such SPECT modalities. Moreover, the arrangement of components and/or the types of components included in the example environment 100 are for illustrative purposes only. For example, the rotating structure 104 (e.g., a rotating gantry) may comprise additional components to support the operation of a radiation source 118 and/or detector array 106, such as a cooling unit, power units, etc. As another example, at least a portion of a data acquisition component 122 may be comprised within and/or attached to the detector array 106.

In the example environment 100, an examination unit 108 of the imaging modality is configured to examine one or more objects 102. The examination unit 108 can comprise a rotating structure 104 and a (stationary) support structure 110, also referred to herein as a frame, which may encase and/or surround as least a portion of the rotating structure 104 (e.g., as illustrated with an outer, stationary ring, surrounding an outside edge of an inner, rotating ring)). During an examination of the object(s) 102, the object(s) 102 can be placed on an object support 112, such as a bed or conveyor belt, for example, that is selectively positioned in an examination region 114 (e.g., a hollow bore in the rotating structure 104), and the rotating structure 104 can be rotated and/or supported about the object(s) 102 by a rotator 116, such as a bearing, motor, belt drive unit, drive shaft, chain, roller truck, etc.

The rotating structure 104 may surround a portion of the examination region 114 and may comprise one or more radiation sources 118 (e.g., an ionizing X-ray source, gamma radiation source, etc.) and a detector array 106 that is mounted on a substantially diametrically opposite side of the rotating structure 104 relative to the radiation source(s) 118.

During an examination of the object(s) 102, the radiation source(s) 118 emits fan, cone, wedge, and/or other shaped radiation 120 configurations from a focal spot(s) of the radiation source(s) 118 (e.g., a region within the radiation source(s) 118 from which radiation 120 emanates) into the examination region 114. It will be appreciated that such radiation 120 may be emitted substantially continuously and/or may be emitted intermittently (e.g., a brief pulse of radiation is emitted followed by a resting period during which the radiation source 118 is not activated).

As the emitted radiation 120 traverses the object(s) 102, the radiation 120 may be attenuated differently by different aspects of the object(s) 102. Because different aspects attenuate different percentages of the radiation 120, an image(s) may be generated based upon the attenuation, or variations in the number of photons that are detected by the detector array 106. For example, more dense aspects of the object(s) 102, such as a bone or metal plate, may attenuate more of the radiation 120 (e.g., causing fewer photons to strike the detector array 106) than less dense aspects, such as skin or clothing.

The detector array 106 can comprise a linear (e.g., one-dimensional) or two-dimensional array of elements (sometimes referred to as pixels or channels) disposed as a single row or multiple rows in the shape of spherical arc, typically having a center of curvature at the focal spot of the radiation source(s) 118, for example. As the rotating structure 104 rotates, the detector array 106 is configured to directly convert (e.g., using amorphous selenium and/or other direct conversion materials) and/or indirectly convert (e.g., using Cesium Iodide (CsI) and/or other indirect conversion materials) detected radiation into electrical signals.

Signals that are produced by the detector array 106 may be transmitted to a data acquisition component 122 that is in operable communication with the detector array 106. Typically, the data acquisition component 122 is configured to convert the electrical signals output by the detector array 106 into digital data and/or to combine the digital data acquired during a measuring interval. The collection of digital output signals for a measuring interval may be referred to as a "projection" or a "view."

The example environment 100 also illustrates an image reconstructor 124 that is operably coupled to the data acquisition component 122 and is configured to generate one or more images representative of the object 102 under examination based at least in part upon signals output from the data acquisition component 122 using suitable analytical, iterative, and/or other reconstruction technique (e.g., tomosynthesis reconstruction, back-projection, iterative reconstruction, etc.).

The example environment 100 also includes a terminal 126, or workstation (e.g., a computer), configured to receive image(s) from the image reconstructor 124, which can be displayed on a monitor 128 to a user 130 (e.g., security personnel, medical personnel, etc.). In this way, the user 130 can inspect the image(s) to identify areas of interest within the object(s) 102. The terminal 126 can also be configured to receive user input which can direct operations of the object examination unit 108 (e.g., a speed of rotation for the rotating structure 104, an energy level of the radiation, etc.).

In the example environment 100, a controller 132 is operably coupled to the terminal 126. In one example, the controller 132 is configured to receive user input from the terminal 126 and generate instructions for the examination unit 108 indicative of operations to be performed.

It will be appreciated that the example component diagram is merely intended to illustrate one embodiment of one type of imaging modality and is not intended to be interpreted in a limiting manner. For example, the functions of one or more components described herein may be separated into a plurality of components and/or the functions of two or more components described herein may be consolidated into merely a single component. Moreover, the imaging modality may comprise additional components to perform additional features, functions, etc. (e.g., such as automatic threat detection).

Figure 2:
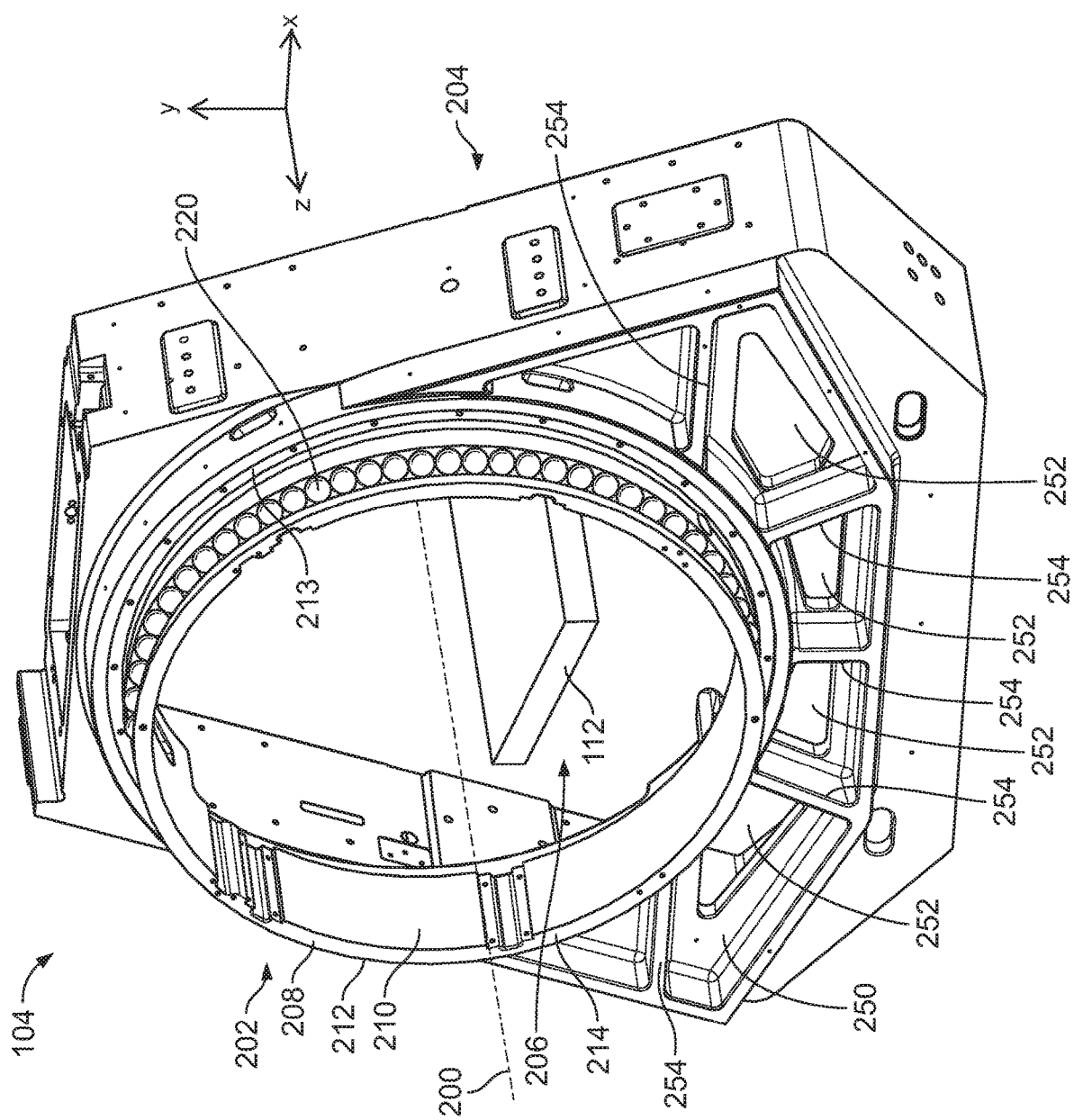
FIG. 2 illustrates an example rotating structure having a first support portion and a second support portion.

FIG. 2 illustrates an example of the rotating structure 104 that can be used within the example environment 100 of FIG. 1. The rotating structure 104 can rotate about an axis 200 (e.g., extending in the z-direction). In an example, the rotating structure 104 comprises a first support portion 202 and a second support portion 204. The first support portion 202 and the second support portion 204 can be attached to each other via fasteners (e.g., screws, rivets, etc.) or can be integrally formed as a one-piece structure. As such, the first support portion 202 and the second support portion 204 can simultaneously rotate about the axis 200. The first support portion 202 and the second support portion 204 may comprise any number of materials, such as metals, non-metals, composites, etc.

In some embodiments, the first support portion 202 defines a substantially cylindrical first interior cavity 206. In an example, the first support portion 202 may comprise a wall 208 that defines the first interior cavity 206. The axis 200 can extend through a center of the first interior cavity 206, such that the wall 208 is separated a substantially constant distance (e.g., a radial distance) from the axis 200 about a circumference of the wall 208. That is, in an example, the axis 200 may be separated from the wall 208 a first distance at a first circumferential location of the wall 208, and a second distance at a second circumferential location of the wall 208. In such an example, the first distance and the second distance may be substantially equal.

The wall 208 comprises an inner radial surface 210 and an outer radial surface 212. The inner radial surface 210 can define a circumference of the substantially cylindrical first interior cavity 206. The outer radial surface 212 may diametrically oppose the inner radial surface 210. That is, in an example, the inner radial surface 210 may be located in closer proximity to the axis 200 than the outer radial surface 212.

The wall 208 comprises an intermediate surface 214 that interfaces with the inner radial surface 210 and the outer radial surface 212. By interfacing with the inner radial surface 210 and the outer radial surface 212, the intermediate surface 214 may form an angle with respect to the inner radial surface 210 and the outer radial surface 212. In an example, the angle may be between about 80 degrees and about 100 degrees, such as by being about 90 degrees. In the illustrated example, the intermediate surface 214 may define an end of the first support portion 202 along the axis 200 that is opposite the second support portion 204.

The first support portion 202 may comprise one or more substantially annular bearings 220 for coupling the rotating structure 104 to the stationary support structure 110. In an example, the substantially annular bearings 220 may be disposed on the outer radial surface 212 of the wall 208. Due to the substantially annular shape of the annular bearings 220 and the substantially annular shape of the outer radial surface 212, the rotating structure 104 can rotate about the axis 200. It may be appreciated that while the annular bearings 220 (e.g., the ball bearings) may be disposed on the outer radial surface 212 and may contact the outer radial surface 212, in some embodiments a bearing support structure that is configured to maintain the position of the annular bearing 220 may be attached to an to an axial surface 213 adjacent the outer radial surface 212. For example, the bearing support structure may be substantially L-shaped, with a first surface of the bearing support structure pressing the annular bearing 220 against the outer radial surface 212 (e.g., the annular bearings 220 are disposed between the first surface of the bearing support structure and the outer radial surface 212) and a second surface of the bearing support structure being secured to the axial surface 213.

Figure 3:
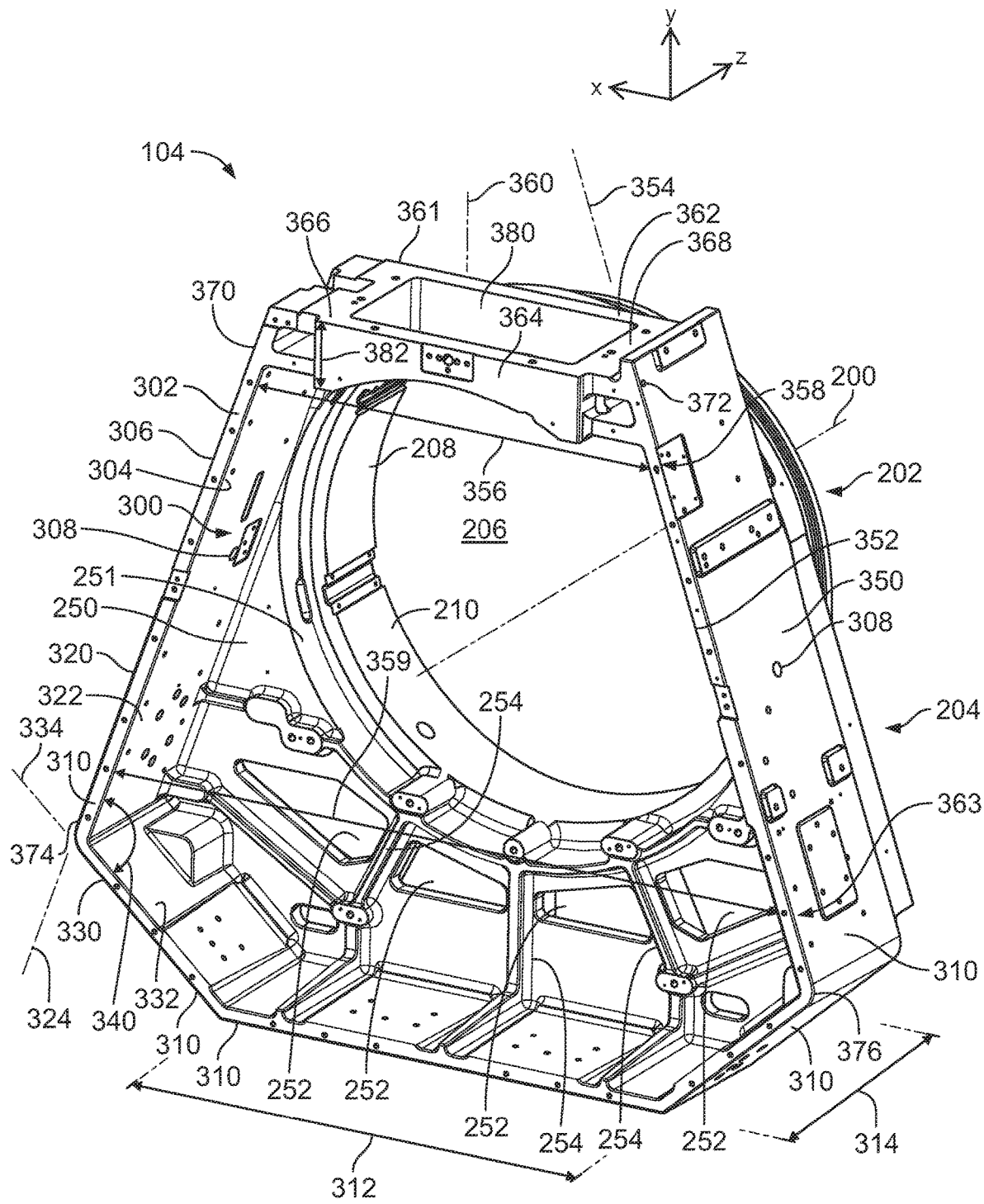
FIG. 3 illustrates an example second support portion of a rotating structure having an interior cavity.

Referring to FIGS. 2 and 3, the first support portion 202 can be attached to the second support portion 204 by an intermediate wall 250. The intermediate wall 250 can lie in a plane that is substantially perpendicular to the axis 200 (e.g., lying in an x,y plane). The intermediate wall 250 can define an opening 251 that substantially matches a size and location of the first interior cavity 206. In an example, the intermediate wall 250 can be attached to or formed with the first support portion 202 at an inner location. The intermediate wall 250 can be attached to or formed with the second support portion 204 at an outer location. As such, due to the attachment between the first support portion 202, the intermediate wall 250, and the second support portion 204, the rotating structure 104 can define a substantially fixed and/or static structure that exhibits reduced or limited deformation, deflection, and/or vibration when the rotating structure 104 is rotated about the axis 200. In some examples, the intermediate wall 250 defines one or more wall openings 252. The wall openings 252 can assist in receiving one or more structures or components that may be attached to the rotating structure 104 and/or can allow for airflow that helps cool components disposed within the second support portion 204 of the rotating structure 104.

In an example, one or more rigid structures 254 may be provided as part of the intermediate wall 250 to increase the rigidity of the intermediate wall 250. In such an example, the rigid structures 254 can extend through the intermediate wall 250 adjacent the wall openings 252. The rigid structures 254 can comprise a thicker and/or denser material than surrounding walls so as to reduce deformation, deflection, and/or vibration between the first support portion 202 and the second support portion 204. In an example, the rigid structures 254 can extend substantially perpendicularly with respect to the axis 200.

Referring to FIG. 3, a rear perspective view of the rotating structure 104 is illustrated. In an example, the second support portion 204 can define a non-cylindrical second interior cavity 300. In an example, the second support portion 204 may comprise a wall 302 that defines the non-cylindrical second interior cavity 300, with the wall 302 extending substantially about the axis 200. The second interior cavity 300 is adjacent to the first interior cavity 206, such that the axis 200 can intersect and extend through both the first interior cavity 206 and the second interior cavity 300.

In an example, the first interior cavity 206 and the second interior cavity 300 can have different, non-matching shapes. For example, the first interior cavity 206 can have a substantially circular shape or cylindrical shape. The second interior cavity 300 can have a non-circular shape or non-cylindrical shaped defined by one or more substantially linear sidewalls. In addition, the first interior cavity 206 can have a different cross-sectional size (e.g., as measured along a plane that is substantially perpendicular to the axis 200) than the second interior cavity 300. For example, a cross-sectional size of the first interior cavity 206 (e.g., an area of the first interior cavity 206) may be less than a cross-sectional size of the second interior cavity 300.

The wall 302 comprises an inner surface 304 and an outer surface 306. The inner surface 304 defines the non-cylindrical second interior cavity 300. The outer surface 306 may diametrically oppose the inner surface 304. That is, in an example, the inner surface 304 may be located in closer proximity to the axis 200 than the outer surface 306 at a location.

The wall 302 may define one or more openings 308 that extend from the inner surface 304 to the outer surface 306. In an example, the opening 308 can define gaps, spaces, cavities, or the like formed within the wall 302. The openings 308 can be provided so as to receive and/or support one or more structures, components, or the like within the wall 302.

The wall 302 may comprise one or more wall segments 310. In an example, a plurality of wall segments 310 may be provided, with adjacent wall segments 310 forming an interior angle that is between about 0 degrees to about 180 degrees. The wall segments 310 in the illustrated example are substantially planar, though the wall segments 310 may have bends, curves, undulations, or other non-planar shapes. In an example, some or all of the wall segments 310 may comprise non-equal lengths 312, 314, such that some wall segments 310 may be shorter or longer in length than other wall segments 310. In other examples, the wall segments 310 may have substantially similar or identical lengths. In this example, the lengths 312, 314 of the wall segments 310 may be defined as extending along a direction that is substantially perpendicular to the axis 200.

While the example second support portion 204 of FIG. 3 comprises six wall segments 310, any number may be provided. The wall segments 310 can extend a distance along the axis 200 (e.g., between an upstream end and a downstream end of the second support portion 204). The size of the wall segments 310 along the axis 200 can function to reduce deformation, deflection, and/or vibration of the rotating structure 104. For example, the wall segments 310 can support one or more structures or components, while being relatively resistant to deformation, deflection, and/or vibration during rotation of the rotating structure 104.

The wall segments 310 comprise a first wall segment 320 and a second wall segment 330. The first wall segment 320 has an inner surface 322 that, in part, defines the second interior cavity 300. In an example, the inner surface 322 of the first wall segment 320 lies in a first plane 324. The second wall segment 330 has an inner surface 332 that, in part, defines the second interior cavity 300. In an example, the inner surface 332 of the second wall segment 330 lies in a second plane 334. In some examples, the first plane 324 and the second plane 334 may be non-parallel.

In an example, an interior angle 340 may be defined by the inner surface 322 of the first wall segment 320 that, in part, defines the non-cylindrical second interior cavity 300, and the inner surface 332 of the second wall segment 330 that, in part, defines the non-cylindrical second interior cavity 300. In an example, the interior angle 340 may be an obtuse angle (e.g., an angle that is between about 90 degrees and 180 degrees). In an example, some or all of the interior angles defined by inner surfaces of adjacent wall segments may be obtuse angles.

The wall segments 310 may comprise a third wall segment 350. The third wall segment 350 has an inner surface 352 that, in part, defines the second interior cavity 300. In an example, the inner surface 352 of the third wall segment 350 lies in a third plane 354. The third plane 354 may not be co-planar with respect to the first plane 324 and/or the second plane 334. In an example, the third plane 354 may extend non-parallel with respect to the first plane 324 and/or the second plane 334.

The third wall segment 350 may diametrically oppose the first wall segment 320 relative to the non-cylindrical second interior cavity 300. In an example, the first wall segment 320 and the third wall segment 350 may be separated a first distance 356 at a first location 358. The first distance 356 may be measured at a location along a second axis 360 (e.g., perpendicular to the second axis 360) that is perpendicular to the axis 200. In an example, the first wall segment 320 and the third wall segment 350 may be separated a second distance 359 at a second location 363. The second distance 359 may be measured at the second location 363 along the second axis 360 (e.g., perpendicular to the second axis 360). In an example, the first distance 356 may be different than the second distance 359. For example, the first wall segment 320 and the third wall segment 350 can have a gradually increasing distance from each other as measured from first ends 370, 372 of the first wall segment 320 and the third wall segment 350, respectively, to second ends 374, 376 of the first wall segment 320 and the third wall segment 350, respectively.

The wall segments 310 may comprise a fourth wall segment 361. The fourth wall segment 361 may extend between the first wall segment 320 and the third wall segment 350. In an example, the fourth wall segment 361 may be attached at a first end to the first wall segment 320 and at a second end to the third wall segment 350.

The fourth wall segment 361 can comprise a first wall portion 362, a second wall portion 364, a third wall portion 366, and a fourth wall portion 368. The first wall portion 362 and the second wall portion 364 can extend substantially parallel to each other and may be spaced apart to partially define a wall opening 380. In an example, the first wall portion 362 and the second wall portion 364 can extend between the first wall segment 320 and the third wall segment 350 (e.g., perpendicular to the second axis 360).

The third wall portion 366 and the fourth wall portion 368 can extend substantially parallel to each other and may be spaced apart to partially define the wall opening 380. In an example, the third wall portion 366 and the fourth wall portion 368 can extend along the axis 200 in a direction that is substantially perpendicular to the first wall portion 362 and the second wall portion 364. In an example, the first wall portion 362 and the second wall portion 364 may have a substantially similar first length, while the third wall portion 366 and the fourth wall portion 368 may have a substantially similar second length. The first length may be greater than the second length, such that the wall opening 380 defined by the wall portions 362, 364, 366, 368 has a substantially rectangular shape.

The first wall portion 362 and the second wall portion 364 can have a thickness 382 that is non-constant along the first length of the first wall portion 362 and the second wall portion 364. For example, the thickness 382 may be larger at ends of the first wall portion 362 and the second wall portion 364 than at a center of the first wall portion 362 and the second wall portion 364. In the illustrated example, the thickness 382 of the first wall portion 362 and the second wall portion 364 may be at a minimum towards a center, while gradually increasing towards ends of the first wall portion 362 and the second wall portion 364 so as to define an arched shape. Such a shape can accommodate for the first interior cavity 206 so as to not impede and/or block the first interior cavity 206.

It will be appreciated that while some wall segments (e.g., 320, 350) of the second support portion 204 may be non-parallel to each other, at least some wall segments of the second support portion 204 may be substantially parallel to each other. For example, the fourth wall segment 361 may be substantially parallel to a wall segment 310 that is diametrically opposed to the fourth wall segment 361 (e.g., a bottom wall segment).

Figure 4:
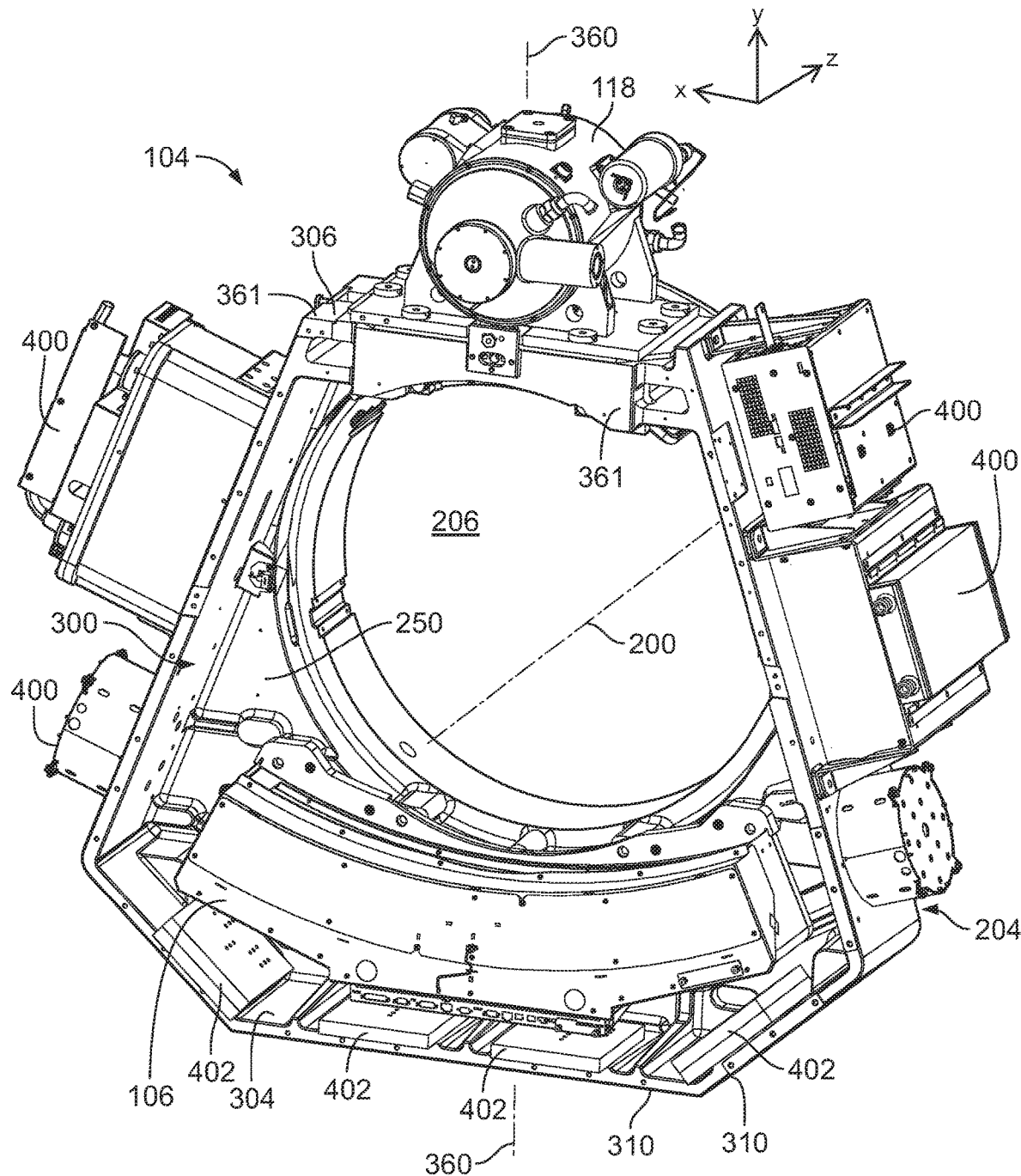
FIG. 4 illustrates an example rotating structure comprising a radiation source and a detector array mounted to a second support portion.

Referring to FIG. 4, the rotating structure 104 is illustrated supporting a plurality of components 400. In an example, the radiation source 118 and the detector array 106 may be mounted to the second support portion 204. For example, the radiation source 118 and the detector array 106 may lie along the second axis 360 that is perpendicular to the axis 200.

The radiation source 118 may be mounted to one of the wall segments 310 of the second support portion 204. For example, the radiation source 118 may be mounted to the fourth wall segment 361 adjacent to and/or received within the wall opening 380 (e.g., illustrated in FIG. 3) defined by the wall portions 362, 364, 366, 368 (e.g., illustrated in FIG. 3). In an example, the radiation source 118 may be mounted to the second support portion 204 on the outer surface 306 of the second support portion 204, and may overlie the wall opening 380 to emit the radiation through the wall opening 380.

The detector array 106 may be disposed within the second interior cavity 300 of the second support portion 204. In an example, the detector array 106 can be attached to the intermediate wall 250 diametrically opposed from the radiation source 118. As such, the detector array 106 and the radiation source 118 may be spaced apart about 180 degrees about the first interior cavity 206. The detector array 106 can be attached to the intermediate wall 250 in any number of ways, such as by fasteners or the like.

Moreover, in some embodiments, a surface of the intermediate wall 250 upon which the detector array 106 is attached can be diametrically opposite a surface of the intermediate wall 250 that abuts the first support portion 202. In this way, for example, the detector array 106 may be spaced apart from the first support portion 202 and/or the annular bearing 220 that are in contact with the first support portion 202. In some embodiments, by spacing the detector array 106 away from the annular bearing few to none of the vibrations caused by the annular bearing 220 are transferred to the detector array 106 and/or those vibrations that are transferred are damped due to the distance between the annular bearing 220 and the detector array 106 and/or the material disposed therein.

In an example, one or more weights 402 may be mounted in the non-cylindrical second interior cavity 300. The weights 402 can be mounted to one or more of the wall segments 310, such as to the inner surface 304 of the wall segments 310. The detector array 106 may be disposed between the radiation source 118 and the weights 402. In an example, the weights 402 can balance and/or offset the weight of the radiation source 118 so as to reduce deformation, deflection, and/or vibration when the rotating structure 104 is rotated about the axis 200.

The object support 112 is configured to convey an object in a direction that is substantially parallel to the axis 200 from an upstream portion of the CT imaging modality to a downstream portion of the CT imaging modality. In an example, the first interior cavity 206 defines an upstream portion of the CT imaging modality while the second interior cavity 300 defines a downstream portion of the CT imaging modality. In another example, the second interior cavity 300 defines the upstream portion of CT imaging modality while the first interior cavity 206 defines the downstream portion of the CT imaging modality.

During an examination, the object support 112 can support an object 102. The object support 112 can be moved within and/or through the first interior cavity 206 defined by the first support portion 202 and the second interior cavity 300 defined by the second support portion 204. As such, the object support 112 can be positioned between the radiation source 118 and the detector array 106. The rotating structure 104 can be rotated about the object support 112 as the radiation source 118 emits radiation into the second interior cavity 300. The radiation 120 may be attenuated by different aspects of the object(s) 102 supported on the object support 112 and detected by the detector array 106.

The size, shape, and/or geometry of the rotating structure 104 can reduce deformation, deflection, and/or vibration that may be experienced by the radiation source 118 and the detector array 106. For example, wall segments 310 of the rotating structure 104 are arranged to form a partially symmetric shape (e.g., symmetric about the second axis 360 but asymmetric about an axis that is perpendicular to the first axis 200 and the second axis 360 and bisects the second support portion 204) that can reduce vibration. Additionally, the wall segments 310 extend a distance along the first axis 200 that provides additional rigidity and strength to the second support portion 204. Further, the rigid structures 254 can extend between the first support portion 202 and the second support portion 204 so as to reduce deformation and/or vibration between the first support portion 202 and the second support portion 204. As a result of the reduced deformation, deflection, and/or vibration, image quality obtained from the detector array 106 may be improved.

It may be appreciated that "example" and/or "exemplary" are used herein to mean serving as an example, instance, or illustration. Any aspect, design, etc., described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form. Also, at least one of A and B or the like generally means A or B or both A and B.

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

What is claimed is:

1. A computed tomography (CT) imaging modality, comprising:
   a radiation source configured to emit radiation;
   a detector array configured to detect at least a portion of the radiation; and
   a rotating structure configured to rotate about an axis, the rotating structure comprising:
      a first support portion defining a substantially cylindrical interior cavity; and
      a second support portion defining a non-cylindrical interior cavity, wherein the radiation source and the detector array are mounted to the second support portion, and
   wherein the first support portion is disposed within the non-cylindrical interior cavity of the second support portion.

2. The CT imaging modality of claim 1, wherein the second support portion comprises a wall segment defining an opening that the radiation source overlies to emit the radiation through the opening, the wall segment comprising a wall portion, defining a portion of the opening, having a non-constant thickness along a length of the wall portion.

3. The CT imaging modality of claim 1, comprising an object support configured to convey an object in a direction parallel to the axis from an upstream portion of the CT imaging modality to a downstream portion of the CT imaging modality, wherein the non-cylindrical interior cavity defines the upstream portion of the CT imaging modality and the substantially cylindrical interior cavity defines the downstream portion of the CT imaging modality.

4. The CT imaging modality of claim 1, wherein the first support portion comprises a substantially annular bearing for coupling the rotating structure to a stationary support structure.

5. The CT imaging modality of claim 4, wherein:
   the first support portion comprises a wall having an inner radial surface defining a circumference of the substantially cylindrical interior cavity and having an outer radial surface diametrically opposing the inner radial surface, and
   the substantially annular bearing is disposed on the outer radial surface.

6. The CT imaging modality of claim 1, wherein the rotating structure comprises an intermediate attachment structure that attaches to the first support portion and the second support portion, the intermediate attachment structure lying in a plane that is substantially perpendicular to the axis, and the intermediate attachment structure being located between the first support portion and the second support portion.

7. The CT imaging modality of claim 1, wherein the detector array is disposed within the non-cylindrical interior cavity of the second support portion.

8. The CT imaging modality of claim 1, wherein:
   the second support portion comprises a wall having an inner surface that defines the non-cylindrical interior cavity and an outer surface diametrically opposing the inner surface,
   the wall defines an opening that extends from the inner surface to the outer surface; and
   the radiation source is mounted to the second support portion on the outer surface and overlies the opening.

9. The CT imaging modality of claim 1, comprising a weight mounted in the non-cylindrical interior cavity.

10. The CT imaging modality of claim 9, wherein the detector array is disposed between the radiation source and the weight.

11. The CT imaging modality of claim 1, wherein:
    the second support portion comprises a wall having an inner surface that defines the non-cylindrical interior cavity,
    the wall comprises a first wall segment and a second wall segment,
    an interior angle is defined by an inner surface of the first wall segment that in part defines the non-cylindrical interior cavity and an inner surface of the second wall segment that in part defines the non-cylindrical interior cavity, and
    the interior angle is an obtuse angle.

12. The CT imaging modality of claim 1, wherein the first support portion and the second support portion are integrally formed.

13. A computed tomography (CT) imaging modality, comprising:
    a radiation source configured to emit radiation;
    a detector array configured to detect at least a portion of the radiation; and
    a rotating structure configured to rotate about an axis, the rotating structure comprising:
       a first support portion comprising a wall defining a substantially cylindrical interior cavity, wherein the wall of the first support portion has an outer radial surface, diametrically opposing the substantially cylindrical interior cavity, that has a circumference; and a second support portion comprising a wall defining a non-cylindrical interior cavity, wherein:

the wall of the second support portion comprises a first wall segment having an inner surface that in part defines the non-cylindrical interior cavity, the inner surface of the first wall segment lying in a first plane;

the wall of the second support portion comprises a second wall segment having an inner surface that in part defines the non-cylindrical interior cavity, the inner surface of the second wall segment lying in a second plane; and the first support portion is disposed within the non-cylindrical interior cavity of the second support portion.

14. The CT imaging modality of claim 13, wherein:
an interior angle is defined by the inner surface of the first wall segment and the inner surface of the second wall segment, and
the interior angle is an obtuse angle.

15. The CT imaging modality of claim 13, wherein:
the wall of the second support portion has an inner surface that defines the non-cylindrical interior cavity and an outer surface diametrically opposing the inner surface,
the wall defines an opening that extends from the inner surface to the outer surface; and
the radiation source is mounted to the second support portion on the outer surface and overlies the opening to emit the radiation through the opening.

16. The CT imaging modality of claim 13, wherein the detector array is disposed within the non-cylindrical interior cavity.

17. The CT imaging modality of claim 13, wherein the radiation source and the detector array are mounted to the second support portion.

18. The CT imaging modality of claim 13, comprising an object support configured to convey an object in a direction parallel to the axis from an upstream portion of the CT imaging modality to a downstream portion of the CT imaging modality, wherein the substantially cylindrical interior cavity defines the upstream portion of the CT imaging modality and the non-cylindrical interior cavity defines the downstream portion of the CT imaging modality.

19. The CT imaging modality of claim 13, comprising an object support configured to convey an object in a direction parallel to the axis from an upstream portion of the CT imaging modality to a downstream portion of the CT imaging modality, wherein the non-cylindrical interior cavity defines the upstream portion of the CT imaging modality and the substantially cylindrical interior cavity defines the downstream portion of the CT imaging modality.

20. The CT imaging modality of claim 13, wherein a substantially annular bearing is disposed on the outer radial surface.

21. A computed tomography (CT) imaging modality, comprising:

a radiation source configured to emit radiation;

a detector array configured to detect at least a portion of the radiation; and a rotating structure configured to rotate about an axis, the rotating structure comprising:

a support portion comprising a wall defining a non-cylindrical interior cavity, wherein:

the wall of the support portion comprises a first wall segment having an inner surface that in part defines the non-cylindrical interior cavity, the inner surface of the first wall segment lying in a first plane, the wall of the support portion comprises a second wall segment having an inner surface that in part defines the non-cylindrical interior cavity, the inner surface of the second wall segment lying in a second plane, the wall of the support portion comprises a third wall segment having an inner surface that in part defines the non-cylindrical interior cavity, the inner surface of the third wall segment lying in a third plane, the third wall segment being disposed in a space between the first wall segment and the second wall segment, the second wall segment diametrically opposes the first wall segment relative to the non-cylindrical interior cavity, the radiation source and detector array lie along a second axis perpendicular to the axis, a distance between the first wall segment and the second wall segment at a first location along the second axis is different than a distance between the first wall segment and the second wall segment at a second location along the second axis; and a second support portion comprising a wall defining a cylindrical interior cavity, wherein the second support portion is disposed within the non-cylindrical interior cavity of the support portion.

* * * * *